(12) United States Patent
Swindale et al.

(10) Patent No.: US 7,203,351 B1
(45) Date of Patent: Apr. 10, 2007

(54) ANALYSIS OF OPTIC NERVE HEAD SHAPE

(75) Inventors: Nicholas V. Swindale, Vancouver (CA); Adeline Chin, Vancouver (CA); Phillip Hetherington, Vancouver (CA)

(73) Assignee: Heidelberg Engineering GmbH, Heidelberg (DE)

( * ) Notice: Subject to any disclaimer, the term of this patent is extended or adjusted under 35 U.S.C. 154(b) by 623 days.

(21) Appl. No.: 10/311,475

(22) PCT Filed: Jun. 16, 2000

(86) PCT No.: PCT/CA00/00728

§ 371 (c)(1), (2), (4) Date: Mar. 26, 2003

(87) PCT Pub. No.: WO01/95790

PCT Pub. Date: Dec. 20, 2001

(51) Int. Cl.
*G06K 9/00* (2006.01)

(52) U.S. Cl. .................. 382/128; 382/168; 351/212

(58) Field of Classification Search ................ 382/128, 382/129, 130, 131, 132, 133, 154, 168, 181, 382/191, 203, 254, 255, 260, 274, 286, 291, 382/305, 308, 321; 351/206, 212; 600/561; 257/99; 378/74
See application file for complete search history.

(56) References Cited

U.S. PATENT DOCUMENTS 5,220,360 A * 6/1993 Verdooner et al. .......... 351/212
5,698,866 A * 12/1997 Doiron et al. ................ 257/99
6,129,682 A * 10/2000 Borchert et al. ............ 600/561
6,276,799 B1 * 8/2001 Van Saarloos et al. ...... 351/206
6,698,885 B2 * 3/2004 Berger et al. ............... 351/206
6,714,672 B1 * 3/2004 Berestov et al. ............ 382/154
6,810,140 B2 * 10/2004 Yang et al. .................. 382/154

OTHER PUBLICATIONS

Ramirez, J., M. et al., "Visualization of the Three-Dimensional Topography of the Optic Nerve Head Through a Passive Stereo Vision Model", *Journal of Electronic Imaging*, US, Spie + IS&T, vol. 8, No. 1, Jan. 1999, pp. 92-97.

Okutomi, M. et al., "Color Stereo Matching and Its Application to 3-D Measurement of Optic Nerve Head", *Proceedings IAPR International Conference on Pattern Recognition*, Aug. 30, 1992.

* cited by examiner

*Primary Examiner*—Matthew C. Bella
*Assistant Examiner*—Seyed Azarian
(74) *Attorney, Agent, or Firm*—Nydegger & Associates

(57) ABSTRACT

Methods and apparatus are provided for analysis of 3-dimensional images of an optic nerve head surface topography. Topographic images of the optic nerve head may be analysed to define a topographic model fitted to the topographic image of the optic nerve head about a centre of analysis. The topographic model is defined using model morphological parameters, and the morphological parameters. In some embodiments, the morphological parameters may be used to detect nerve fibre damage or pathology, such as in the diagnosis of glaucoma.

10 Claims, 6 Drawing Sheets

ANALYSIS OF OPTIC NERVE HEAD SHAPE

FIELD OF THE INVENTION

The invention relates to methods of topographic analysis of optic nerve head shape, including computational image analysis techniques, which may for example be applied in the diagnosis of glaucoma using a scanning laser ophthalmoscope.

BACKGROUND

Glaucoma is a slow and irreversible neuro-degenerative disease whose onset is usually not detected by the patient. Diagnosis may be based on a combination of variables (Quigley, *New England Journal of Medicine:* 328:1097–1106 (1993); Sommer. *Eye:* 10:295–30 (1996)) but the most dependable single index is probably the identification of a characteristic pattern of visual field defects. However these defects may only appear after a substantial amount of retinal damage has occurred (Pederson & Andserson, *Arch Ophthalmol.* 98:490–495 (1980); Quigley et al., *Arch Ophthalmol* 100:135–146 (1982); Sommer et al., *Arch Ophthalmol:* 97:1444–1448 (1979), Sommer et al., *Arch Ophthalmol:* 109:77–83 (1991)). There is a widely accepted need therefore for methods which may be used to detect glaucomatous damage. Ideally, such a test would have high sensitivity and specificity and be quickly and cheaply administered to large numbers of the normal population, especially those most likely to be at risk of the disease, such as the elderly and those with a family history of glaucoma.

A variety of scanning laser ophthalmoscopes are known, such as shown in U.S. Pat. No. 4,765,730; U.S. Pat. No. 4,764,006 and U.S. Pat. No. 4,768,873 (all of which are incorporated herein by reference). For example, the Heidelberg Retina Tomograph (HRT) is a confocal laser scanning microscope which may be used for acquisition and analysis of three-dimensional images of the posterior segment of the eye (the fundus). In operation, to acquire digital confocal images, a laser beam is focused on the retina. Oscillating mirrors provide periodic deflection of the laser beam to facilitate sequential scanning of a two-dimensional field of the retina, in which the reflectance at a number of points is measured. To obtain confocal images, light reflected at the adjusted focal plane is measured, to the exclusion of out-of-focus light, to provide a two-dimensional confocal image of an optical section of the retina at the focal plane. A series of optical section images may be acquired, with different focal planes, resulting in a layer-by-layer three-dimensional image. The distribution of reflected light in the three-dimensional image may be assessed to compute the retinal surface height at each point. The matrix of height measurements may be visualized as a topographic image which reflects the three-dimensional retinal surface. In some commercial embodiments, the Heidelberg Retina Tomograph uses a diode laser with a wavelength of 670 nm, and may be used to acquire a three-dimensional image as 32 consecutive and equidistant optical section images, each consisting of 256×256 picture elements. The size of the field of view may be set to 10°×10°, 15°×15°, or 20°×20°. Topographic images may be computed from the acquired three-dimensional images, in which the topographic image consists of 256×256 individual height measurements which are scaled for the individual eye examined.

The Heidelberg Retina Tomograph has been used to obtain three-dimensional images of the surface topography of the optic nerve head (ONH) (Weinreb et al., *Int Ophthalmol:* 13:25–27 (1989); Kruse et al., *Ophthalmology:* 96:1320–1324 (1989); Dreher et al., *Am J Ophthalmol.* 111:221–229 (1991); Cioffi et al., *Ophthalmology;* 100: 57–62 (1993); Mikelberg et al., *J. Glaucoma.* 2:101–103 (1993); Lusky et al., *J. Glaucoma.* 2:104–109 (1993); Rohrschneider et al., *Graefes Arch Clin Exp Ophthalmol.* 231: 457–464 (1993), Rohrschneider et al. *Ophthalmology.* 101: 1044–1049 (1994); Bartz-Schmidt et al., *Ger J Ophthalmol* 3:400–405 (1994); Chauhan et al., *Am J Ophthalmol.* 118: 9–15 (1994); Janknecht and Funk, *Br J Ophthalmol.* 78:760–768 (1994); Orgul et al., *Arch Ophthalmol.* 114: 161–164 (1996)). In moderate and advanced cases of glaucoma this damage leads to anatomical changes in the morphology of the optic disc region, including enlargement of the depression on the centre of the disc, known as the cup. A number of studies has shown that morphological indices calculated from images of the ONH differ significantly between normal eyes and eyes with glaucomatous visual field defects (Burk et al, *Kin Monatsbl Augenheilkd.* 198: 522–529 (1991); Brigatti & Caprioli, *Arch Ophthalmol.* 113:1191–1194 (1995); Mikelberg et al., *J Glaucoma.* 4:242–247 (1995); Weinreb et al., *Am J Ophthalmol.* 120: 732–738 (1995); Brigatti et al., *Am J Ophthalmol.* 121: 511–521 (1996); Uchida et al., *Invest Ophthalmol Vis Sci.* 37:2393 –2401 (1996); Hatch et al., *Br J Ophthalmol.* 81:871–876 (1997); lester et al., *J Glaucoma.* 6:78–82 (1997a); lester et al., *Can J Ophthalmol.;* 32:382–388 (1997b); lester et al., *Ophthalmology* 104:545–548 (1997c); Anton et al., *Am J Ophthalmol.* 125:436–446 (1998); Bathija et al., *J Glaucoma* 7:121–127 (1998); Wollstein et al., *Ophthalmology.* 105:1557–1563 (1998)). Parameters calculated from combinations of these indices can be used to diagnose the presence of glaucomatous field loss, within the populations from which normative values were obtained, with sensitivities and specificities that are typically in the range of 80–90%.0

These methods typically rely on shape parameters which are calculated by software following an initial stage in which a technician or clinician uses a computer input device such as a mouse to manually outline the edge of the optic disc. This outlining process has been controversial because different observers do not always agree where the disc margins should be placed and this introduces an element of uncontrolled variability into the morphological analysis (Orgul et al., *Graefes Arch Clin Exp Ophthalmol.* 235:82–86 (1997)). Thus, while the art provides a method for interpretation of scanning laser ophthalmoscope 3-dimensional images of ONH surface topography, there is typically a manual component that introduces variability and requires the time and efforts of a skilled technician. There is therefore a need for image processing techniques that may be automated so that they do not require this kind of manual intervention.

Images of normal and glaucomatous optic nerve heads obtained with the scanning laser ophthalmoscope typically exhibit a central, roughly circular depression of variable width and depth (the cup), superimposed on a relatively smooth surface with a variable degree of curvature (the rim region). This curvature is almost always convex, and is caused by the layer of ganglion cell axons becoming, of geometrical necessity, increasingly thick as the axons converge towards the optic nerve.

SUMMARY OF THE INVENTION

In accordance with various aspects of the invention, methods and apparatus are provided for analysis of 3-dimensional images of an optic nerve head surface topography. In various embodiments, the methods and apparatus of the invention may be used to automate diagnostic analysis of the optic nerve head. In some embodiments, the invention provides methods and apparatus based on parametric mathematical modelling of optic nerve head shape. The analysis may proceed by finding, for each image, one or more model parameters which produce the greatest degree of similarity between a topographic model and the acquired topographic image of the optic nerve head. The parameter values may then be used as descriptors of optic nerve head morphology, and may also be used as a basis for further morphological analysis. In some embodiments, the analysis of optic nerve head topography images in accordance with the invention may be used to provide a method for detection of nerve fibre damage or pathology, such as the diagnosis of glaucoma.

In one aspect, the present invention provides methods that allow optic nerve head images to be classified objectively by an automated procedure that does not require prior manual outlining of disc boundaries. The present invention may provide particularly advantageous embodiments when the methods of the invention are automated. Automation of the system of the invention is facilitated by the adoption of an approach that includes identifying a centre of analysis of the optic nerve model, rather than defining an area within which the optic nerve is found. In this way, the topographic modelling of the optic nerve head may proceed based on the identification of a centre of analysis, whereas previous approaches have required a human operator to identify an area within which the optic nerve may be found. As such, the automated methods of the invention are not dependent on subjective estimates of the position of the borders of the optic disc, estimates which may vary within and between operators and complicate the comparison of studies done in different centres.

Parameters identified by the model of the invention as being particularly useful in indicating glaucomatous damage to the optic disc include the horizontal and vertical components of image curvature, i.e. the amount by which the nerve fibre layer surrounding the cup bulges upwards into the vitreous, and the steepness of the cup walls. Cup size and other measures of surface irregularity in the region of the cup are also informative. Accordingly, one or more of the model morphological parameters or indices of the invention may be compared to one or more corresponding predetermined morphological parameters or indices obtained from one or more control topographic images, the predetermined morphological parameters or indices may be calculated using the methods of the invention, or alternative methods. In accordance with this aspect of the invention, methods of diagnosing glaucoma are provided comprising determining morphological parameters of the topographic model of a subject's optic nerve head, such as vertical curvature and steepness of cup walls.

In one aspect, the invention provides a method of characterizing an optic nerve head, and an apparatus for implementing the method, the method comprising:
 a) acquiring a topographic image of the optic nerve head;
 b) defining a topographic model fitted to the topographic image of the optic nerve head about a centre of analysis, wherein the centre of analysis is identified on the optic nerve head, and wherein the topographic model is defined using model morphological parameters.

The topographic model may be applied to identify a cup on the topographic image of the optic nerve head, wherein the cup includes the centre of analysis. The topographic model may include a parabolic surface and the acquired topographic image may be compared to the parabolic surface to identify the cup region on the acquired topographic image, and the cup region may include the centre of analysis of the optic nerve head. The method may further include the steps of: a) excluding the cup region from the acquired image and refitting the parabolic surface to the acquired image; and, b) modelling the shape of the cup superimposed on the model parabolic surface, to define the topographic model of the optic nerve head.

BRIEF DESCRIPTION OF THE FIGURES

In drawings which illustrate embodiments of the invention,

FIG. 4(*c*) shows one-dimensional profile through a model image along the horizontal axis, at $y=y_0$, illustrating the meaning of some of the model parameters. Parameter c describes the overall curvature of the image in the horizontal axis; s determines the steepness of slope of the cup walls; $z_m$ is a measure of cup depth; $r_0$ is the distance of the cup wall (at half-height) from the center of the cup at $x_0$. $z_0$ is the baseline height of the image (all depth measures are relative to $z_0$).

DETAILED DESCRIPTION OF THE INVENTION

Figure 1:
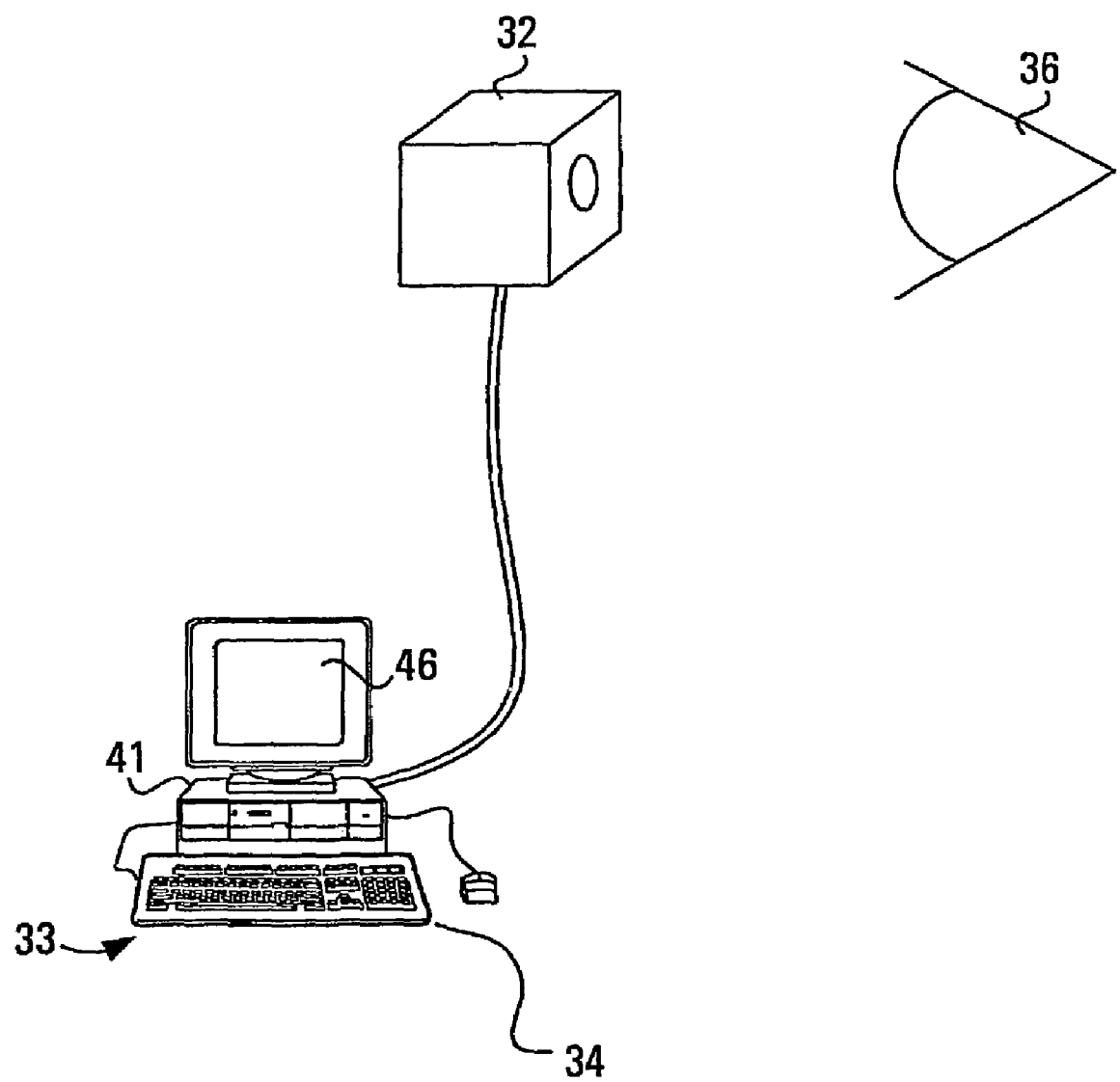
FIG. 1 is a schematic illustration of an automated embodiment of the invention, in which a computer is provided to define a topographic model of the optic nerve head.

FIG. 1 schematically illustrates an apparatus for acquisition and analysis of information according to an embodiment of the invention. The apparatus may include a computer, shown generally at 33, operable to receive digital information, such as images from a scanning laser ophthalmoscope 32, for producing images of an eye 36. In accordance with alternative aspect of the invention, the topography of the ONH may be measured using ultrasound apparatus, or by any other means for acquiring a topographic image of the optic nerve head Referring to FIG. 2, computer 33 is shown in greater detail and includes a processor circuit shown generally at 41. In this embodiment, processor circuit 41 includes processor 40 and an I/O port 42 for receiving images from the scanning laser ophthalmoscope 32 shown in FIG. 1. By way of example, Processor 40 can be selected from the Intel x86 chipset, Intel Pentium™ series, Motorola PowerPC™ or G3 series, or another suitable processor. The processor circuit 41 may also include a data store 43 in communication with and accessible processor 40. Data store 43 may be comprised of volatile memory such as Random Access Memory (RAM), and non-volatile memory such as a hard disk drive or Read Only Memory (ROM). The data store 43 may include a hard drive having an image store area 48 and a program store area 50. The program store area 50 may hold programs for directing processor 40 to receive images at the image I/O port 42 and to store such images in the image store 48. Program store 50 may contain a variety of software programs, including an operating system, which may for example be selected from a variety of operating systems providing a graphical user interface (GUI) such as in Microsoft Windows 98™, Windows CE™, Windows NT™, Macintosh Operating System 9™ or a UNIX operating system.

Processor 40 may be connected to a display unit 46, which may be any type of display supporting the display of graphical images, such as a monitor, a liquid crystal display (LCD), a digital screen or other electronic display device. Processor 40 may also be connected to a user input device 34, such as a keyboard or the like. In addition, the processor 40 may be connected to a communications I/O port 44 for connection to a modem and ultimately the internet, for example, for receiving images which may also be stored in the image store 48 or for receiving programs which may be stored in the program store 50. In addition, the processor may be in communication with a media interface 52 such as a CD ROM drive or a floppy diskette drive, for example, for receiving images or programs for storage in the image store area 48 or program store area 50 respectively.

Figure 3:
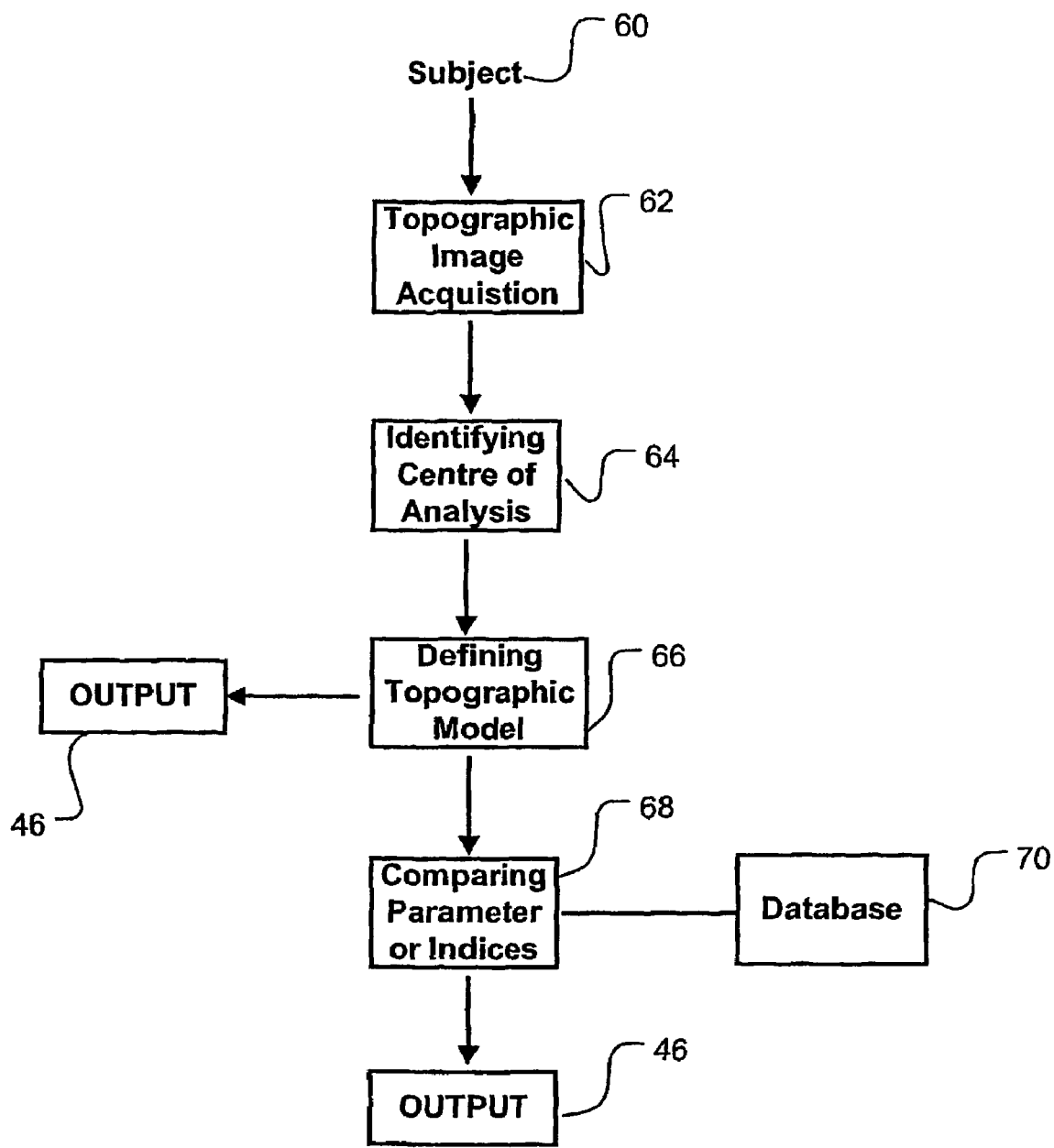
FIG. 3 is a schematic illustration of the methods of the invention.
Figure 4:
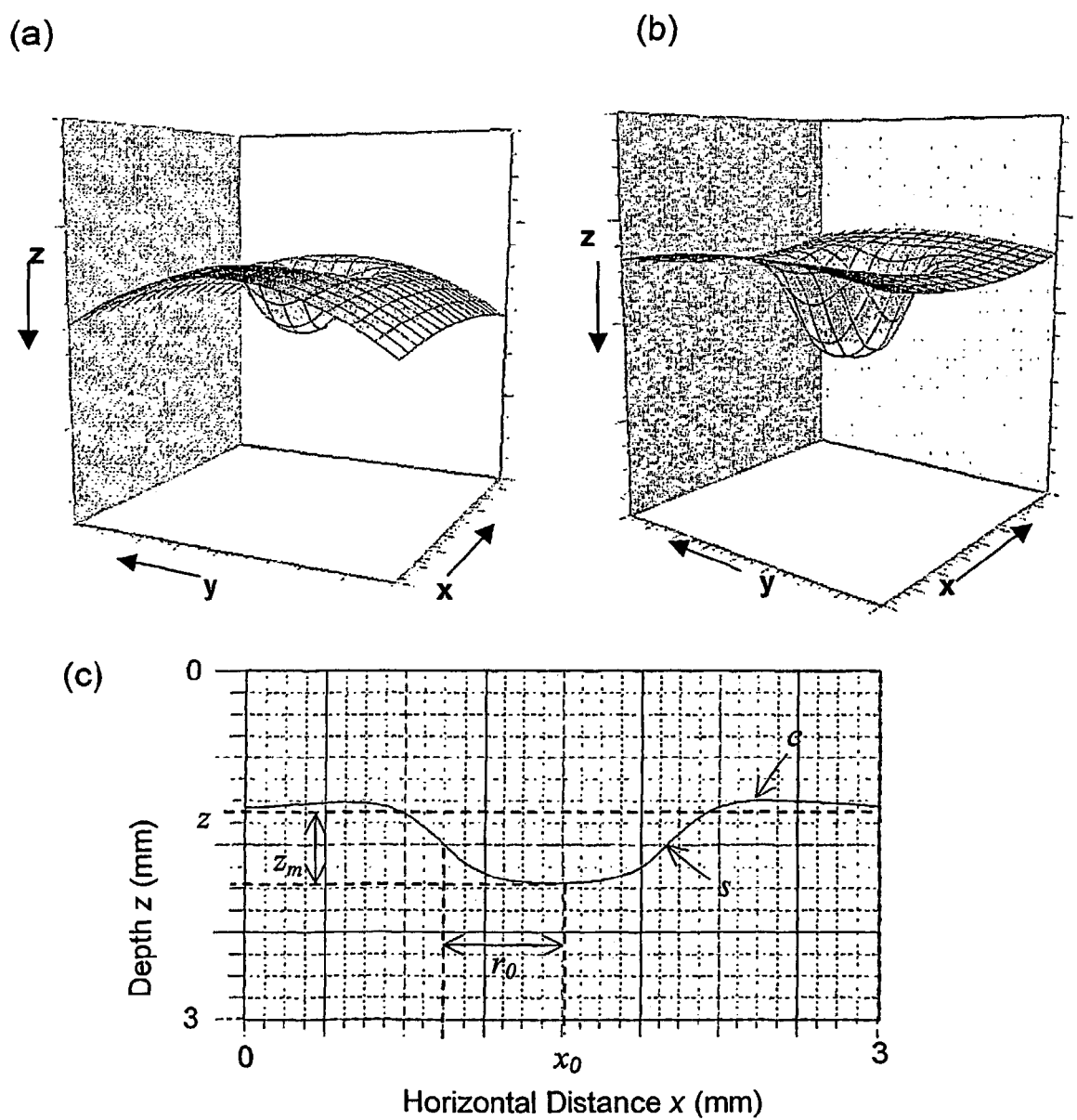
FIG. 4 shows, in (a) & (b), wire-mesh plots of model ONH profiles based on mean parameter values from (a) normal images and (b) glaucomatous images. Each of the three axes is approximately 3 mm long.
Figure 5:
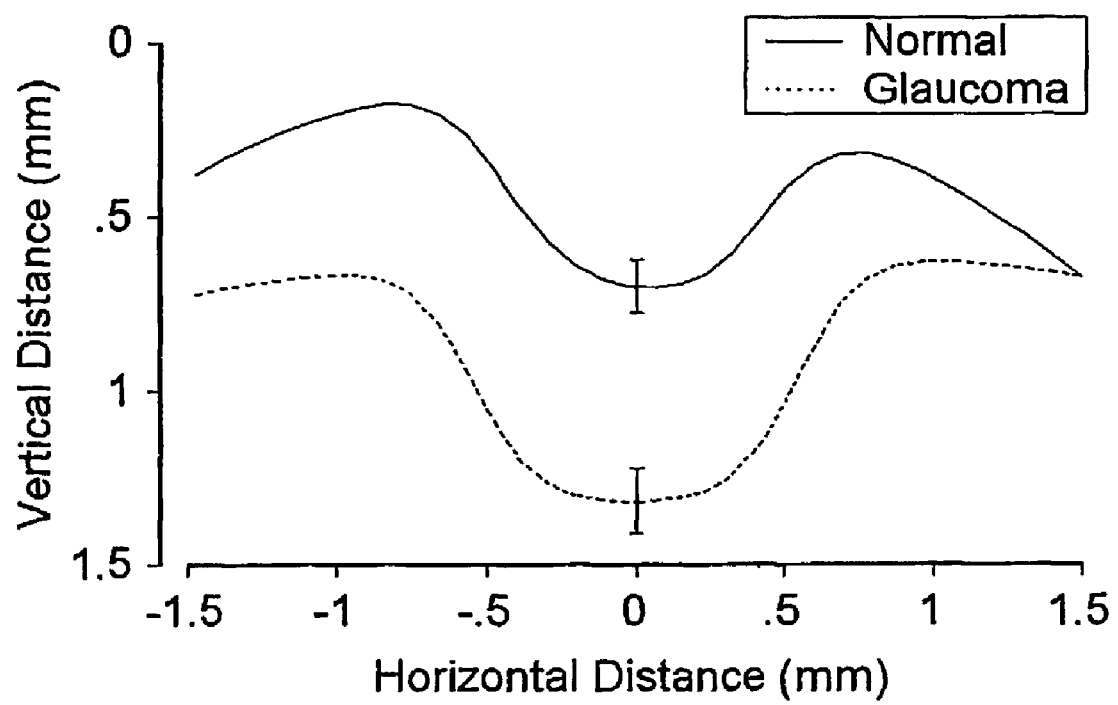
FIG. 5 shows one-dimensional profiles through the model function at $y=y_0$ i.e. along the horizontal axis through the center of the model cup. The parameters used to calculate the profiles are the means from the normal and glaucoma populations. The vertical offset between the two profiles is arbitrary and was chosen so that they did not cross. Error bars show the r.m.s. difference between each image and its corresponding model, averaged across all the images in each group.
Figure 6:
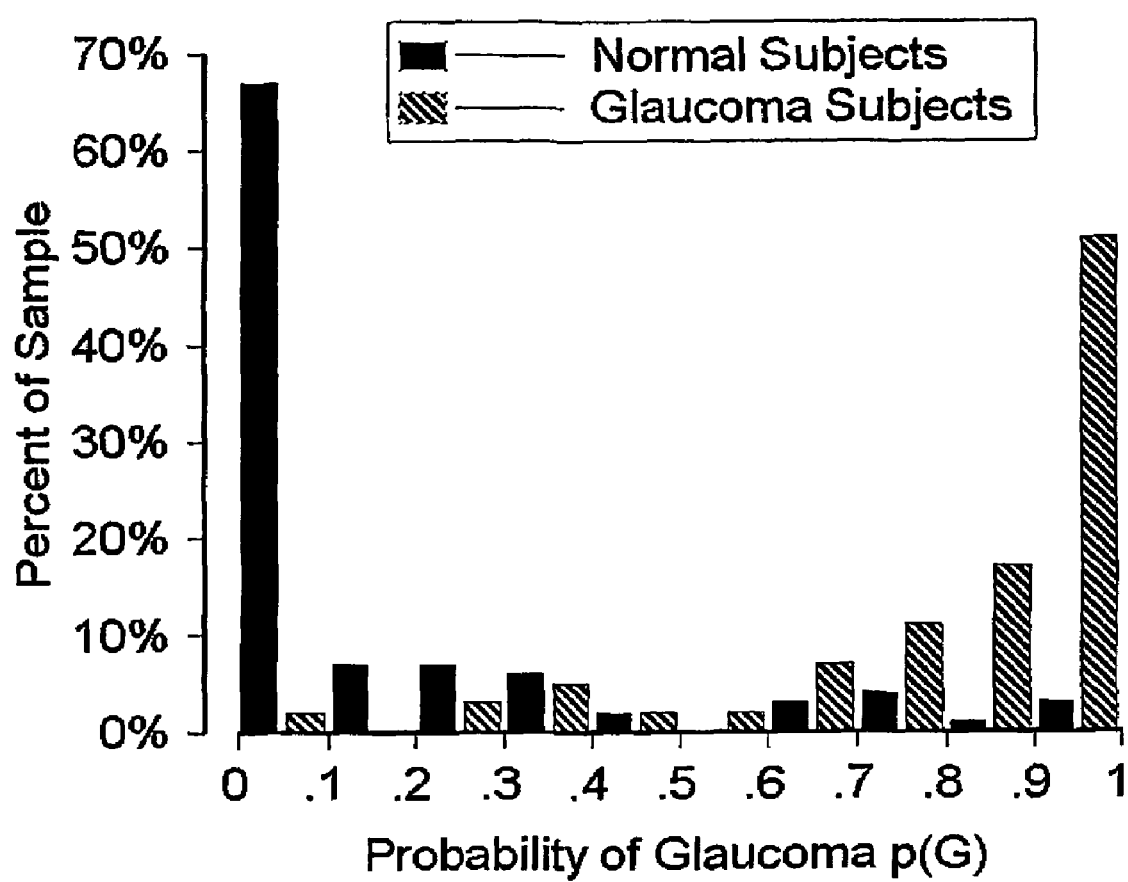
FIG. 6 shows the distribution of the values of p(G) in the normal and glaucoma groups of the Example, the calculated probability that an ONH image is from an eye with glaucoma obtained with classification methods of the invention.

FIG. 3 schematically illustrates a process for characterizing an optic nerve head, as may be carried out by processor 40. The illustrated process involves a first block of codes 62 which directs the processor to acquire topographic images of eye 36 from an input device such as scanning laser ophthalmoscope 32. Topographic image acquisition is followed by block 64 which directs the processor to identify a centre of analysis. Block 66 directs processor 40 to define a topographic model of the acquired topographic image. The topographic model may for example be output on display 46 for analysis (examples of topographical models are shown in FIGS. 4 and 5). Topographic models output in this way may for example be used in diagnosis of pathologies such as glaucoma. Block 68 may be used to direct processor 40 to compare morphological parameters or indices, for example to provide output as shown in FIG. 6. Morphological parameters derived from the topographical model produced by processor 40 may be compared to one or more corresponding predetermined morphological parameters (or morphological indices) obtained from one or more control topographic images and stored, for example, in database 70. The predetermined morphological parameters may be in the form of statistical information derived from prior analysis of normal and abnormal ONH images.

In accordance with the invention, a variety of mathematical models may be used to provide a topographical model of the ONH. In some embodiments, such mathematical models may have a relatively small number of parameters, which may simplify interpretation of the parameters in anatomical terms. In one embodiment, the invention provides the following mathematical model:

$$z(x, y) = \tag{1}$$

-continued
$$\frac{z_m}{1 + e^{(r-r_0)/s}} + a(x - x_0) + b(y - y_0) + c(x - x_0)^2 + d(y - y_0)^2 + z_0$$

where $r = \sqrt{(x-x_0)^2 + (y-y_0)^2}$ \hfill (1a)

This defines the depth of the surface, z, as a function of position (x, y) on the surface. Movement in the positive x direction may be identified with movement in the nasal direction (i.e. away from the fovea), and movement in the positive y direction may be set to correspond to movement towards superior retina. The first term on the left hand side of the equation represents a circularly symmetric cup, centred on position $(x_0, y_0)$, with a depth $z_m$, a radius $r_0$, and with walls with a slope inversely proportional to s (the smaller the value of s, the steeper the slope). The following four terms in the equation describe a surface with variable slant in the x and y directions (parameters a and b respectively) and with variable curvature, assumed to be parabolic, in the x and y direction. Because of the parabolic terms, the model may become less faithful to the retinal surface at progressively larger distances from the centre of the cup, such as distances larger than about 1.5–2 mm. Table 1 identifies a number of morphological parameters that may be obtained using formula (1) in one embodiment.

TABLE 1

Description of Model Parameters

| Name | Symbol | Description |
|---|---|---|
| naso-temporal slant | a | overall component of tilt in the naso-temporal axis (mm/mm) |
| vertical slant | b | overall component of tilt along the vertical axis (mm/mm) |
| horizontal image curvature | c | overall curvature along the naso-temporal axis (mm²/m) |
| vertical image curvature | d | overall curvature in the vertical direction |
| cup position | $x_0, y_0$ | position of center of cup in image (mm) |
| cup radius | $r_0$ | distance from center of cup to the cup wall at half-height (mm) |
| cup slope | s | slope of cup wall (mm) |
| cup depth | $z_m$ | depth of the cup (mm) |
| vertical offset | $z_0$ | offset of the image in the vertical direction (mm) |

It will be appreciated that a wide variety of alternative equations may be used to model the topography of the ONH in accordance with the present invention. The parabolic terms in equation (1), for example, may be adopted to simplify analysis, while higher order equations may be used to improve the fit of the model or to offer alternative model parameters for comparison purposes. In the foregoing model, certain symmetries of the model are adopted for simplicity, whereas alternative models may forego such symmetries in favour of improved fit or alternative parameters. Radial functions may for example provide an alternative model, and the assignment of x and y axis to horizontal and vertical co-ordinates may be varied.

For each image, the 10 free parameters of equation (1) may be adjusted to give the best fit of the model to the acquired topographical image. Fit, f, may be defined as the root mean square of the difference between the image and the model, measured in millimeters:

$$f = \left\{ \frac{1}{N} \sum_{i,j}^{allpixels} [yI(i,j) - z(\alpha i, \beta j)]^2 \right\}^{\frac{1}{2}} \quad (2)$$

where I (i, j) is the value of the image at pixel (i, j) and N is the total number of pixels in the image. α and β, which are normally equal, scale pixel indices in the i and j directions, to millimeters in the x and y directions respectively, and y scales the one byte per pixel value in the image (0–255) to millimeters in the depth (z) dimension. Alternative measures of fit may be adopted in alternative embodiments of the invention.

In some embodiments, the fitting process may be accomplished in two stages: first, an initial rough estimate of the 10 free parameter values of equation (1) may be made and secondly, a refinement of the values to minimize f may be carried out, for example using an iterative non-linear least-squares fitting procedure. The initial rough estimate may be accomplished via the following set of steps:

1) calculation of a least-squares fit to the image of just the last five terms of equation (1) (i.e. of the parabolic surface). Because this function is linear in its 5 parameters it is possible to calculate the best fitting parameter values explicitly using standard methods (Press et al., *Numerical recipes: the art of scientific computing*. 2$^{nd}$ edn. Cambridge University press, Cambridge, UK (1994)).

2) This function may then be subtracted from the acquired image, to obtain a surface in which the cup is a major feature. The average of the positions and values of the 50 largest (i.e. deepest) pixel values in this surface may then be calculated, or an alternative number in alternative embodiments, to obtain estimates of cup position ($x_0$, $y_0$) and depth ($z_m$) respectively. A region of pixels, equal to $\frac{1}{10}^{th}$ of the image width, along the edges of the image may be excluded when doing the search for deep pixels.

3) The fit of the parabolic surface may then be repeated, this time excluding the region of the image identified as the cup, such as a region within a distance of 0.5 mm from the estimated centre of the cup. This fit may then be used to obtain an initial estimate of a, b, c, d and $z_0$. The initial estimates of cup radius and slope may be fixed, such as at 0.5 mm and 0.1 respectively. Following this, the parameter estimates may be further refined, for example using the Levenburg-Marquardt optimisation technique (Press et al., 1994).

It will be appreciated that the refinement of the positioning of the centre of analysis using the foregoing approach may be avoided in some embodiments, where a satisfactory fit is achievable without resorting to the cup-subtraction routine. In embodiments which forego the cup-subtraction process, the centre of analysis may be positioned in accordance with the best fit of the parabolic parameters (or alternative ONH parameters in embodiments that utilize an equation other than a parabolic equation to describe the ONH).

The image analysis process of the invention may be applied, for example, to 10°×10° acquired images. The acquired images may be extracted from databases, such as databases created by the operating software (version 2.01) provided with the Heidelberg Retina Tomograph. The program HRTCOMP may for example be used to extract the images and the program DBSCALES may be used to extract the appropriate scaling parameters (α, β and γ) for each image. Because the edges of the images sometimes contains artifacts, a region typically along each edge of the image may be excluded from analysis, such as a region 10 pixels wide. In addition, to decrease processing time, 256×256 pixel images may be reduced in size by averaging over blocks of 4×4 pixels, to give 60×60 pixel images. Averaging over smaller blocks, or not averaging at all, may be used in alternative embodiments.

Following the function fits and derivation of parameter values, several additional morphological indices may be calculated. The selection and definition of these indices may for example be guided by their usefulness in discriminating between normal and glaucomatous images. Examples are set out in Table 2.

TABLE 2

Description of Secondary Parameters

| Name | Symbol | Description |
|---|---|---|
| cup gradient measure | $g_r$ | overall steepness of cup walls |
| cup gradient measure temporal | $g_r^T$ | overall steepness of cup walls on the temporal side |
| cup gradient measure nasal | $g_r^N$ | overall steepness of cup walls on the nasal side |
| fit in central region | $f_R$ | dissimilarity between the model and image in the cup region |
| fit of parabolic function | $f_p$ | dissimilarity between the image from a smooth parabolic surface lacking a cup |
| maximum cup depth | $z_{500}$ | average of the 500 largest depth values in the cup |

In one embodiment, a set of pixels, R, which include the cup may be defined with a centre position ($x_0$, $y_0$) and a radius=$r_0$+$\log_e(9)$s. Within this region, cup depth is greater than 10% of its value at the centre. The calculations may be carried out on the raw, 256×256 pixel acquired images. As described above for the fits, pixels on a defined border along the edges of the image may be excluded from R. The following values may then be calculated:

1) the goodness of fit, defined as $$f_R = \left\{ \frac{1}{N} \sum_{i,j \in R} [yI(i,j) - z(\alpha i, \beta j)]^2 \right\}^{\frac{1}{2}} \quad (3)$$

where N is the number of points contained in R. The larger the value of $f_R$, the worse is the fit of the model to the image in the region of the cup. As described below, this value may be significantly larger in eyes with glaucoma;

2) an index of the steepness of the cup walls. Although parameter s (equation 1) gives a measure of steepness, an alternative measure may be obtained by summing the image gradient values within R. This may be done with two further modifications (a) only the radial component of the gradient i.e. the component measured in the direction pointing towards the centre of the cup, is used, and (b) only gradient values with large negative slope values less than −45° are included in the sum. The gradient is defined in terms of its x and y components as $$G_x(i, j) = \frac{\gamma[I(i+1, j) - I(i, j)]}{\alpha};$$

$$G_y(i, j) = \frac{\gamma[I(i, j+1) - I(i, j)]}{\beta}.$$
(4)

The radial component $G_r$ is given by $$G_r = \frac{(x - x_0)G_x + (y - y_0)G_y}{|r|},$$
(5)

Since depth is measured as a positive quantity, the steeper the slope of the cup walls, the more negative will be the radial gradient values. The measure used here, defined as the positive quantity $g_r$, is given by $$g_r = \log_e \left\{ \sum_{i,j \subset R} thr(-G_r, 1) \right\}$$
(6)

where thr (x, 1) equals x, if x>1, and equals 0 if x<1. $g_r$ is therefore the log of the sum of all those radial gradient values within region R which are more negative than, i.e. steeper than, a gradient of −1 mm/mm. (The log was taken in the exemplary embodiment described herein because the resulting distribution of values more closely approximated a normal distribution).

In a similar manner, separate indices for gradients in the nasal and temporal halves of region R may be calculated, denoted by parameters $g_r^N$ and $g_r^T$ respectively.

3) An index of maximum cup depth, defined as the average of the 500 largest depth values, measured within region R is calculated. Denoting this average as $I_{500}$ we define the index as $$z_{500} = \gamma I_{500} - z_0$$
(7)

4) The fit to the image of a curved surface lacking a cup (i.e. equation (1), but without the first term on the left hand side) is calculated, by analogy with equation (2), and may be denoted by $f_p$. This value is low in normal images in the exemplified embodiment, particularly those in which the cup is small or absent.

In one aspect, the invention provides for steps of comparing morphological parameters or indices derived from the methods of the invention with predetermined morphological parameters or indices obtained from a control image or population. In alternative embodiments, the predetermined indices may be obtained from a control normal population or from other populations, such as populations with defined degrees of damage to the optic nerve e.g. early glaucoma patients. For example, a given set of D parameters measured from each image, i.e. a data vector $x = (x_1, x_2, \ldots x_D)$, the probability may be calculated that the point came from a control (normal) group i.e. p (x|N), and may be compared to the probability that it came from a glaucoma group i.e. p(x|G). These probabilities may be calculated using the multivariate normal probability density function (Bishop, *Neural networks for Pattern recognition*. Oxford University Press (1998)):

$$p(x) = \frac{1}{(2\pi)^{\frac{D}{2}} |C|^{\frac{1}{2}}} \exp\left\{ -\frac{1}{2}(x - u)^T C^{-1}(x - u) \right\}$$
(8)

where u is the mean of x taken over the group in question (normal or glaucomatous) and C is the within-group covariance matrix. When cross-validation is used, data from the case being classified may be excluded from the data used to calculate the means and the covariance matrices. This may give a less biased estimate of the ability of the classification method to generalize to new data i.e. data not used to derive the classification method in the first place.

In accordance with the exemplified embodiment, the probability that acquired topographic image measurements were from an eye with glaucoma have been calculated i.e. p(G|x). According to Bayes' theorem (Bishop, 1998) this is $$p(G \mid x) = \frac{p(x \mid G)p(G)}{p(x \mid N)p(N) + p(x \mid G)p(G)}$$
(9)

where p(N) and p(G) are the prior probabilities that the case in question is normal or has glaucoma. In the exemplified embodiment, the prior probabilities were 0.5 because the sample sizes (=100) were equal, but this will not necessarily be the case with unequal sample sizes or if the normal population is being screened. Images may for example be classified as glaucomatous if p(G|x)>0.5 and is normal if p(G|x)<0.5.

EXAMPLE 1

As an example of the application of the invention, analysis was performed on a database of 100 images obtained from the eyes screened to exclude the presence of glaucoma, and 100 images obtained from eyes with open angles and showing visual field changes indicative of glaucoma. Criteria for subject selection are described in more detail in the following section. The model fitting, analyses and classification are implemented with the aid of a batch processing language which allowed the calculations to be done on each of the images in an automated fashion, without user intervention. To avoid the possibility of artefactual differences between the groups, images from normal and glaucoma patients are intermingled in the analysis sequence. Computations were performed using a 233 MHz Pentium II PC.

Criteria for Subject Selection

1) Volunteers for the normal group were excluded:
 (a) if they had eye disease or a history of eye disease known to be related to glaucoma (e.g. pigmentary dispersion syndrome);
 (b) if they had a condition such as keratoconus or cataract which would be likely to interfere with scanning;
 (c) if they did not have normal corrected visual acuity; or
 (d) if they were strabismic (which often causes fixation difficulties during scanning).

2) If they passed the screening questions, the following tests were then done:
 (a) a brief medical history was taken, including details of any relative(s) who had glaucoma;
 (b) a Humphrey visual field test (threshold 30-2) of both eyes was done; and (c) intraocular pressure (IOP) was measured in both eyes by applanation tonometry; and finally (d) HRT scans, 10°×10° in size, of each eye were obtained, through undilated pupils. To obtain these images, at least 3 separate scans of each ONH were obtained and a single mean of 3 images was calculated (Weinreb et al., *Arch Ophthalmol.* 111:6+36–638 (1993)). When more than 3 scans were done, the set of 3 giving the lowest standard deviation, as reported by the HRT software, was chosen.

3) Following these tests, eyes were excluded from the normal group if:

(a) the visual field was outside normal limits as defined by the Humphrey Glaucoma Hemifield Test; some borderline subjects on this test were included after further clinical evaluation of their fields;

(b) there were >30% fixation losses during testing;

(c) the IOP was above 20 mm Hg;

(d) the standard deviation obtained on averaging 3 separate HRT scans was greater than 50 μm. A family history of glaucoma was not used as a criterion for exclusion. As it turned out, many (33/100) of the volunteers did report a positive family history, and this was often the reason that subjects gave for volunteering in the first place.

4) In order to more closely age-match the normal group with the glaucoma group, some younger subjects were excluded from analysis.

5) In cases where scans from both eyes of each subject were available, only one was chosen for inclusion in the final database. This was done either at random, or in such a way as to make the numbers of left and right eyes equal.

Glaucoma Subjects

Glaucoma subjects were patients with open angles, and whose visual fields (Humphrey or SITA 30-2) indicated glaucomatous damage. Following Mikelberg et al. (1995) the criteria used for inclusion were the presence of (a) three adjacent points down by 5 dB with one of the points being down by at least 10 dB;

(b) two adjacent points down by 10 dB; or (c) three adjacent points just above or below the nasal horizontal meridian down by 10 dB.

None of the points could be edge points except those immediately above or below the horizontal meridian. The field taken closest in time to the HRT scan was used for evaluation. In almost all cases this was within at least 6 months of examination by the HRT. The results of HRT scans, and/or other types of ONH examination, were excluded as criteria in making the classification of glaucoma, in order to make the prediction of visual field test results on the basis of ONH morphology more objective. However, abnormal ONH appearance was often a reason for the initial referral of the patient to the clinic. IOP was not used as a criterion for exclusion/inclusion because it may be normal in glaucoma (often as a result of ongoing treatment). As with the normal subjects, HRT images were obtained as the means of three separate scans, through undilated pupils. Images with a standard deviation >50 μm were excluded from analysis. In cases where both eyes satisfied the criteria for inclusion, the eye showing the lesser degree of visual field damage was chosen. If no other criteria applied, eyes were chosen so as to equalize the number of left and right eyes in the sample.

Table 3 lists the patient and normal subject demographics for the two groups.

TABLE 3

Subject Demographics

| | | Normal | Glaucoma |
|---|---|---|---|
| Number | | 100 | 100 |
| Age | range | 25–87 yrs | 27–81 yrs |
| | mean & s.d. | 53 ± 14 yrs | 61 ± 13 yrs |
| Gender | male | 43 | 51 |
| | female | 57 | 49 |
| Eye | R | 48 | 51 |
| | L | 52 | 49 |
| Race | Caucasian | 94 | 87 |
| | Asian | 6 | 12 |
| | Black | 0 | 1 |
| Mean Deviation | | 0.3 ± 1.6 dB | −4.9 ± 2.7 dB |
| s.d. of HRT scans | | 0.024 ± 0.008 mm | 0.029 ± 0.010 mm |
| Refraction | | −0.48 ± 2.1 D | −0.61 ± 2.4 D |

To compare the automated methods of the invention with the accuracy of classification obtained using manual HRT parameters, all the images were outlined manually using standard Heidelberg software (version 2.01) and the resulting 14 global shape parameters were entered into a spreadsheet. The discriminant function analysis done by Mikelberg et al. (1995) was then repeated for comparison with the present method. SPSS (V7.5) was used to do the analysis.

Non-linear least-squares optimization of parameters is dependent on good initial estimates and may fail to produce meaningful results if the initial estimates are poor (Press et al., 1994) or if the model itself if not a good one. For each image we therefore checked that the fitting procedure had produced what seemed likely to be correct values, particularly with respect to cup position ($x_0$ and $y_0$) and cup depth ($z_m$). This was done by visually examining the model and real images to check that they seemed similar, and cup position was close to the position of the real cup, and by examining parameters to make sure that they were within expected ranges. Acceptable fits and parameter values were judged to have been obtained in 198 out of the 200 images. The two images in which the automated procedure failed were from normal eyes in which a cup was barely detectable. In one of these images an acceptable fit was obtained by manually choosing initial parameters. In the other image a fit was obtained by manually choosing initial parameters. In the other image a fit was obtained by constraining $z_{max}=0$ and setting $x_0$ and $y_0$ equal to the estimated centre of the cup, close to the middle of the image. Radius and slope values were set equal to the means of the rest of the normal group for the purposes of calculating the other derived parameters in this image.

Figure 2:
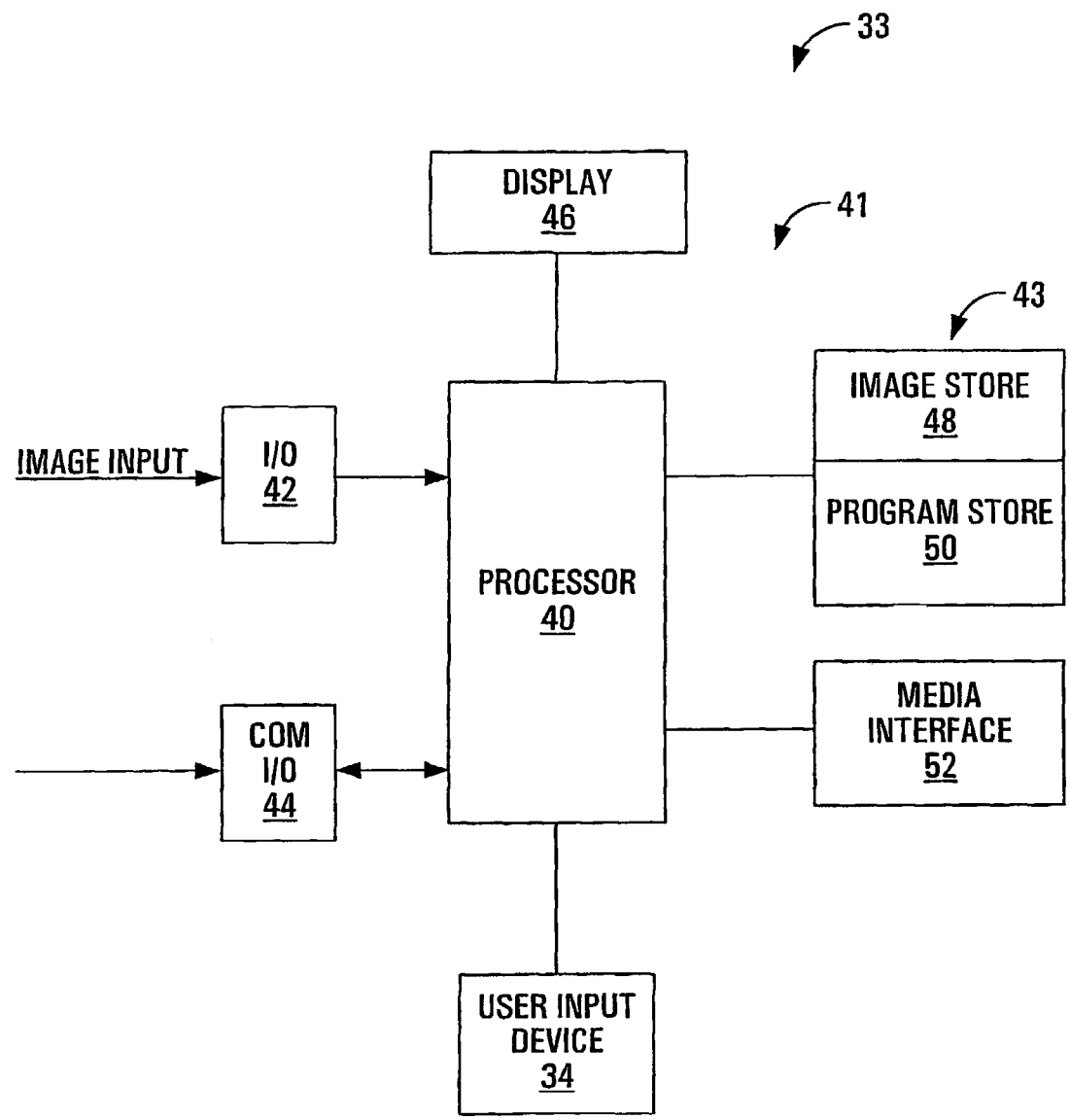
FIG. 2 is a schematic illustration of the automated processing arrangement of an embodiment of the invention.

Table 4 gives the means and standard deviations of the model parameters, and Table 5 gives corresponding values for the morphological indices derived from them, for both the normal and glaucoma groups. The tables also show a statistical measure of the differences between the groups, $d^1$, expressed in standard deviation units. The rows in each table are in decreasing order of $d^1$, i.e. decreasing statistical difference between the measures in the two groups. A one-way ANOVA was done and this showed that in almost all cases the differences were statistically significant ($p<0.001$). The final column, on the right hand side of each table, shows the Pearson correlation coefficient, r, between each parameter and age, measured in the normal group. FIG. 2 illustrates one-dimensional model profiles, taken along the x-axis at $y=y_0$, calculated using the averages of the parameters for the normal group (solid line) and with the averages for the glaucoma group (dashed line).

TABLE 4

Model Parameters

| Symbol | Description | Normal | Glaucoma | d[1] | r (age) |
|---|---|---|---|---|---|
| c | horizontal image curvature | 0.193 ± 0.091 | 0.051 ± 0.053 | −1.97*** | 0.16 |
| d | vertical image curvature | 0.045 ± 0.075 | −0.049 ± 0.046 | −1.55*** | 0.23** |
| a | naso-temporal slant | −0.093 ± 0.130 mm/mm | 0.018 ± 0.097 mm/mm | 0.98*** | 0.002 |
| f | fit of the model to the image | 0.076 ± 0.021 mm | 0.092 ± 0.024 mm | 0.71*** | −0.061 |
| $r_0$ | cup radius | 0.444 ± 0.142 mm | 0.547 ± 0.154 mm | 0.70*** | −0.064 |
| $z_m$ | cup depth | 0.621 ± 0.249 mm | 0.739 ± 0.222 mm | 0.50*** | −0.372*** |
| b | vertical slant | 0.008 ± 0.072 mm/mm | −0.01 ± 0.068 mm/mm | −0.26 | 0.005 |
| s | cup slope | 0.116 ± 0.059 | 0.107 ± 0.055 | −0.16 | −0.163 |
| $z_0$ | vertical offset | 0.982 ± 0.312 mm | 1.028 ± 0.339 mm | 0.14 | 0.209** |

** = p < .01
*** = p < .001

TABLE 5

Secondary Morphological Indices

| Symbol | Description | Normal | Glaucoma | d[1] | r (age) |
|---|---|---|---|---|---|
| $g_r^T$ | cup gradient measure temporal | 8.39 ± 0.58 | 9.06 ± 0.47 | 1.28*** | −0.15 |
| $g_r$ | cup gradient measure | 9.35 ± 0.49 | 9.90 ± 0.40 | 1.23*** | −0.18 |
| $g_r^N$ | cup gradient measure nasal | 8.85 ± 0.48 | 9.31 ± 0.38 | 1.06*** | −0.17 |
| $f_R$ | fit in central region | 0.107 ± 0.038 mm | 0.147 ± 0.048 mm | 0.93*** | −0.20** |
| $f_p$ | fit of parabolic function | 0.137 ± 0.047 mm | 0.178 ± 0.054 mm | 0.81*** | −0.29** |
| $z_{500}$ | maximum cup depth | 0.702 ± 0.247 mm | 0.878 ± 0.250 mm | 0.71*** | −0.31** |

** = p < .01
*** = p < .001

The exemplified embodiment of the model generally gave a good description of the acquired images, especially in the normal group, where the value of the fit (the root mean square of the difference between the model and real image) averaged 0.076 mm. This was also evident from visual comparisons. The fact that the fit in the glaucoma group, which averaged 0.095 mm, is less good, suggests a correlation between glaucoma and irregularity in cup shape, and means that the value of the fit may be used to discriminate between normal and glaucomatous images.

Two of the model parameters in the exemplified embodiment showing the greatest difference between the two groups were c and d (equation 1) which measure the curvature of the image, minus the model cup, in the x (horizontal or naso-temporal) and y (vertical or superior-inferior) directions respectively. In the majority of normal images both curvature values are positive. These values may reflect rim volume, i.e. the increase in thickness of the retinal nerve fibre layer as the axons converge towards the centre of the disc. These measurements further show that curvature may be greater in the horizontal axis of controls than it is in glaucoma groups. In normal subjects the vertical component of curvature may be smaller than the horizontal component, and in a minority of normals its value may be negative. This component is also substantially reduced in the glaucoma group of this example, where the mean value is negative.

The slant parameter, b, which measures net slant in the vertical direction, did not differ significantly from zero, and did not differ significantly between the two groups in this example. The other slant parameter, a, which measures slant along the naso-temporal axis, averaged −0.093 mm/mm (=5.30) in normal subjects, and this was significantly different from zero. In the exemplified sample of glaucoma subjects this height difference disappeared and, on average, slant values did not differ significantly from zero.

The measures of cup depth ($z_m$) and radius ($r_0$) were both increased in the glaucoma group, although these differences were not as large as those for curvature and naso-temporal slant. The model's measure of the slope of the cup walls (s, which is inversely related to the steepness) was slightly smaller in the glaucoma group, reflecting an increased steepness of the walls of the cup. However the difference is not statistically significant in the exemplified group.

The values of $f_p$—the goodness of fit to the image of a model lacking a cup i.e. a parabolic surface—were also analysed. The fits were relatively poor in most cases, with the exception of images (almost always from normal subjects) in which the cup was poorly defined. Values of $f_p$ differed significantly between the two groups and were found to increase the accuracy with which images could be classified. The value of $f_p$ was lowest in normal eyes in which a cup was barely detectable or absent. As it can be calculated without the need for initial guesses of parameter values, a low value of $f_p$ (e.g. <0.075 mm) may in some embodiments be used to identify images lacking a cup, which may be excluded from further processing on this basis.

Although the model of this example describes normal and abnormal discs relatively well, and many of the model parameters differ significantly between groups, the exemplified model does not describe some significant features of glaucomatous discs, in particular the noticeably increased steepness of the cup walls. Additional morphological indices may be derived from the acquired images, using the model parameters as a framework for the calculations, to provide additional basis for analysis and diagnosis.

The centre of the model cup, its radius and slope may be used to define a central circular region of the image, denoted R, which just encloses the cup and its walls. Visual checks may be made to determine whether any part of a cup appears to fall outside of this region, which they did not in the exemplified group, nor in most cases did the region greatly increase the cup in size. As an example, three measures of steepness were calculated, one for the whole region ($g_r$), one for the nasal half of the region ($g_r^N$) and one for the temporal half ($g_r^T$). Table 5 shows that, in the normal group of this example, the nasal gradient measure was larger than the temporal gradient measure. However the temporal measure differed more between the normal and the glaucoma groups.

An additional measure of goodness of fit was made: $f_R$ measured the fit of the model function within R. This value was significantly larger on average in images from the glaucoma group (Table 5).

In some embodiments, the measure of cup depth, $z_m$, may be relatively insensitive to small local excavations in the bottom of the cup which could be indicative of glaucoma. A depth measure of the average of the 500 deepest values measured within region R (which typically contained 2,500–3,000 pixels) may be used to assess this characteristic. This measure, $z_{500}$, with d'3=0.76, proved to differ more between the two groups than did $z_m$, for which d'=0.52.

The effect of age on the parameters was examined in the normal group by calculating the Pearson correlation between each parameter and age. The results are shown in Tables 4 and 5. Age had a significant effect on cup depth, where the correlation (r=−0.372, slope=−0.0068 mm/yr) indicates a decrease in depth with increasing age. A smaller positive correlation between age and the horizontal and vertical components of curvature was also found. In almost every case in this example, the effects of age, although small in magnitude, were in the opposite direction from those of glaucoma. This may make the detection of glaucoma easier in older subjects.

Not all parameters need be used for the purpose of classifying images. In this example, those which showed little difference between the groups were excluded, namely, s, $z_0$ and b. Some sets of parameters were closely related (e.g. $z_m$ & $z_{500}$, f & $f_R$, and $g_r$, $g_r^N$ & $g_r^T$) and for these parameters we took as an example the one showing the largest difference, as measured by d', between the two groups. One parameter, horizontal image slope (a) was excluded because its inclusion was found to make classification worse and because the difference between the two groups might be artefactual (see below). This resulted in a set of 7 parameters, defined as $x=\{c, d, z_{500}, g_r^T f_P, f_R, r_0\}$. These were used to calculate, for each image, the probability (defined by equations (8) and (9)), that it came from the glaucoma group, i.e. p(G|x). Cases were classified as glaucoma if p(G|x)>0.5. Since p(G|x)=1−p(N|x) this is equivalent to the condition that p(G|x)>p(N|x). When this is done, specificity (the percentage of normal cases correctly classified) and sensitivity (the percentage of glaucoma cases correctly classified) tend to be similar, and equal to the overall classification accuracy.

The distribution of p(G|x) values for the normal and glaucoma populations showed that most cases were correctly classified with high confidence levels (i.e. p>0.9 or <0.1). Table 6 shows the distribution of probability values and of classification mistakes. The overall classification accuracy was 89% (specificity=89%, sensitivity=88%). As might be expected, the accuracy varied with the confidence level of the classification. When the confidence level was low, i.e. for p values between 0.4 and 0.6 (leftmost column of Table 4), the accuracy was 67% (4/6 cases). For high confidence levels, i.e. p>0.9 or <0.1 (rightmost column of Table 4) the overall accuracy was higher at 96% (118/123 cases). Eighty-seven percent of cases were classified with p values >0.7 or <0.3. Within this group, the overall accuracy was 92%.

TABLE 6

Classification Statistics

| range of p values | 0.4 < p < 0.6 | 0.6 < p < 0.7 0.3 < p < 0.4 | 0.7 < p < 0.8 0.2 < p < 0.3 | 0.8 < p < 0.9 0.1 < p < 0.2 | 0.9 < p < 1.0 0.0 < p < 0.1 |
|---|---|---|---|---|---|
| number of cases | 6 | 21 | 25 | 25 | 123 |
| number of mistakes | 2 | 8 | 7 | 1 | 5 |
| % correct | 67% | 62% | 72% | 96% | 96% |
| Cumulative | 0.0 < p < 1.0 | 0.6 < p < 1.0 0.0 < p < 0.4 | 0.7 < p < 1.0 0.0 < p < 0.3 | 0.8 < p < 1.0 0.0 < p < 0.2 | 0.9 < p < 1.0 0.0 < p < 0.1 |
| % of total cases | 100% | 97% | 87% | 74% | 62% |
| % correct | 89% | 89% | 92% | 96% | 96% |

A leave-one-out cross-validation procedure may be carried out to evaluate a classification method, in which data from the case being classified is not used in the calculation of group means and covariance values. This may give a better estimate of a method's ability to generalise to new cases, i.e. cases not used to derive the classification function. With this procedure, six additional wrong classifications were identified and the overall accuracy of the method was reduced to 86%. However, of the new mistakes, three had p(G) values that fell in the 0.4 to 0.6 range, two had values in the 0.2 to 0.4 range and only one had p(G)>0.7. Overall the accuracy of the confidently classified cases was reduced to 88%.

We examined, retrospectively, those images that had been confidently mis-classified by the procedure (i.e. those with p<0.1 or p>0.9) as well as the corresponding visual fields. This included 3 normal and 2 glaucoma subjects (FIG. 6). The clinical interpretation of the normal cases was that two of them had large discs, suggesting that the large cups were a consequence of large disc size. The interpretation of the third disc was that it was suspicious, although the visual field was normal. In both confident false negative glaucoma cases, the clinical interpretation was of normal disc appearance despite glaucomatous visual fields. The observation that the false positives had large discs suggested that this might account for some of the other false positive results.

Analysis of disc area (i.e. the HRT parameter ag) showed that disc area in the 11 false positives was 3.07±0.570 mm2 and this was significantly larger (p<0.001) than the area in the correctly classified normal subjects, which was 2.335±0.578 mm2.

The accuracy of the exemplified method was compared to that which could be obtained from a set of 14 shape parameters calculated by the Heidelberg operating software. The discriminant analysis formula of Mikelberg et al. (1995) which is incorporated into the softwareV2.01 gave a sensitivity of 49% and a specificity of 98%. Adjusting the classification threshold to give more equal values yielded a sensitivity of 77% and a specificity of 77%. An alternative comparison is to subject the data to a new discriminant analysis. Thirteen of the parameters [ag (disc area) was excluded because it is derived from mr (mean radius)] were entered into a forward stepping discriminant analysis, using an F-to-enter of 4.0 and an F-to-remove of 3.0. The overall accuracy was 84% and the cross-validated accuracy was 83.5%. The 6 parameters selected by the analysis were abr (area below reference), mhc (mean height of contour), mr (mean radius), var (volume above reference), vas (volume above surface) and vbr (volume below reference).

For the present example, the correlations were calculated, across both normal and glaucoma groups, between the model parameters and the HRT parameters, and with the visual field mean defect (MD). Table 7 shows the values for some selected HRT and model parameters. The HRT measure of disc area (ag) did not correlate strongly with any of the model parameters, because the model does not provide an explicit estimate of disc area. The highest correlation (r=0.54) was with the fit of the parabolic function ($f_p$). However there was also a strong correlation (r=0.52) with the model's measure of cup radius ($r_0$) which can be explained because cup area and disc area are known to be strongly correlated in normal discs (Teal et al., *Trans Am Ophthalmol Soc.* 70:164 (1972); Bengtsson, *Acta Ophthalmol.* (54:804 (1976); Britton et al., *Am J Ophthalmol.* 103:497–504 (1987)). There was a strong correlation (r=0.94) between the model's measure of cup depth ($Z_{500}$) and the corresponding HRT measure (mdg). $f_p$ (fit of parabolic surface) also correlated strongly (r=0.94) with this measure because the value of $f_p$ will be small when a cup us absent, and therefore its value largely reflects cup depth.

Both $Z_{500}$ and r0 (cup radius) showed weak correlations with HRT parameters hvc and var, on which the shape of the cup would be expected to have little effect.

The model parameter which correlated most strongly (r=0.40) with csm (cup shape measure) was temporal gradient measure, $g_r^T$, however the correlation with cup diameter ($r_0$) was nearly as strong (r=0.37). The correlation between each parameter and the visual field mean defect (MD) was also calculated. These values are also given in Table 7 (second row from the bottom). The parameter showing the highest correlation with MD was c (horizontal image curvature; r=0.51). The HRT indices showing the strongest correlations were abr (area below reference; r–0.43), var (r=–0.48) and mhc (r=–0.41).

The alternative model parameters may be subjected to a received operating characteristic (ROC) analysis, using the methods described in lester et al. (Can. J. Ophthalmol., 32,382–388 (1997)). Values for comparison with the HRT parameters are given in the bottom row of Table 7. In this example, the parameter showing the highest area under the curve (a measure of discrimination between two groups) was the horizontal curvature measure (area=0.93). However, the best HRT measure, mhc (area=0.91) was almost as good. Cup shape measure did less well, with an area=0.77.

Before discussing the interpretation of these shape changes in more detail, we will consider first the limitations of the mathematical modelling method we have used and, secondly, the limitations imposed by the study design.

TABLE 7

Correlations with standard HRT parameters, visual field Mean Deviation and ROC areas

|      | ag    | abr   | mhc   | hvc   | mdg   | csm   | var   | vbr   | $r_0$ | $z_{500}$ | c     | d     | $g_r^r$ | $f_R$ | $f_p$ |       |
|------|-------|-------|-------|-------|-------|-------|-------|-------|-------|-----------|-------|-------|---------|-------|-------|-------|
| Abr  | 0.68  |       |       |       |       |       |       |       |       |           |       |       |         |       |       | abr   |
| Mhc  | 0.22  | 0.34  |       |       |       |       |       |       |       |           |       |       |         |       |       | mhc   |
| Hvc  | −0.04 | −0.36 | −0.22 |       |       |       |       |       |       |           |       |       |         |       |       | hvc   |
| Mdg  | 0.48  | 0.70  | 0.32  | 0.03  |       |       |       |       |       |           |       |       |         |       |       | mdg   |
| Csm  | 0.21  | 0.41  | 0.12  | −0.21 | 0.18  |       |       |       |       |           |       |       |         |       |       | csm   |
| Var  | 0.12  | −0.52 | −0.29 | 0.73  | −0.27 | −0.25 |       |       |       |           |       |       |         |       |       | var   |
| Vbr  | 0.51  | 0.82  | 0.24  | −0.19 | 0.66  | 0.31  | −0.38 |       |       |           |       |       |         |       |       | vbr   |
| $r_0$ | 0.52 | 0.58  | 0.20  | −0.12 | 0.31  | 0.37  | −0.10 | 0.43  |       |           |       |       |         |       |       | $r_0$ |
| $z_{500}$ | 0.52 | 0.66 | 0.24 | 0.13 | 0.94 | 0.19 | −0.13 | 0.64 | 0.32 |         |       |       |         |       |       | $z_{500}$ |
| C    | −0.34 | −0.64 | −0.53 | 0.54  | −0.47 | −0.27 | 0.62  | −0.41 | −0.44 | −0.32     |       |       |         |       |       | c     |
| d    | −0.30 | −0.60 | −0.53 | 0.38  | −0.58 | −0.22 | 0.57  | −0.42 | −0.28 | −0.39     | 0.84  |       |         |       |       | d     |
| $g_r^r$ | 0.51 | 0.78 | 0.31 | −0.16 | 0.75 | 0.40 | −0.40 | 0.61 | 0.51 | 0.78     | −0.55 | −0.55 |         |       |       | $g_r^r$ |
| $f_R$ | 0.37 | 0.60 | 0.21 | 0.09 | 0.85 | 0.18 | −0.20 | 0.59 | 0.33 | 0.82     | −0.34 | −0.44 | 0.68    |       |       | $f_R$ |
| $f_p$ | 0.54 | 0.72 | 0.25 | 0.07 | 0.94 | 0.28 | −0.18 | 0.72 | 0.44 | 0.94     | −0.38 | −0.45 | 0.77    | 0.83  |       | $f_p$ |
| MD   | −0.09 | −0.43 | −0.41 | 0.32  | −0.27 | −0.23 | 0.48  | −0.24 | −0.29 | −0.20     | 0.55  | 0.48  | −0.46   | −0.27 | −0.26 | MD    |
| RO   | 0.60  | 0.85  | 0.91  | 0.74  | 0.73  | 0.77  | 0.85  | 0.84  | 0.69  | 0.69      | 0.93  | 0.86  | 0.82    | 0.76  | 0.73  | ROC area |
|      | ag    | Abr   | mhc   | hvc   | mdg   | csm   | var   | vbr   | $r_0$ | $z_{500}$ | c     | d     | $g_r^r$ | $f_R$ | $f_p$ |       |

The particular mathematical model of this example is not the only one that could be used. Its two main components: a circularly symmetric cup placed on a background with parabolic curvature may be varied in alternative models adapted to reproduce the range of ONH shapes encountered in normal subjects. Real cups are often not circularly symmetric. Modelling an asymmetric may be accomplished with the introduction of additional shape parameters. In the model of the example, the parabolic curvature of the background (i.e. the rim and disc margins) leads to depth values which increase as the square of the distance from the centre of the cup, which does not happen in reality over a large distance. The function of the example is adapted for images which are 10°×10° in size and do not extend outside the region in which the retinal nerve fibre layer is becoming increasingly thick as fibres converge towards the optic nerve. Alternative models may be adapted to work on larger (e.g. 15°×15° images).

The method described above can be extended to take into account the fact that the cup may be elongated, rather than circular in shape. The original model equation, which may be referred to as 'the circular model', can be elaborated by including two new parameters, e and $\theta_e$, which describe the amount of elongation, and its angle, respectively. What will be referred to as 'the elliptical model' is described as follows. The equation describing the shape of the optic nerve head and cup is similar to the original method (c.f. equation 1):

$$z(x, y) = \frac{z_m}{1 + e^{(r-r_0)/s}} + a(x - x_0) + b(y - y_0) + c(x - x_0)^2 + d(y - y_0)^2 + z_0 \quad (A1)$$

As before, this gives z, the depth of the surface, as a function of position (x, y) on the surface. Parameters $x_0$ and $y_0$ specify the centre of the cup; $z_m$ is the maximum depth of the cup, s is inversely proportional to the slope of the cup walls, a and b give the slant of the background in the x and y directions respectively, and c and d describe the curvature, assumed to be parabolic, in the x and y directions. $z_0$ is a constant offset of the image in the z direction.

As before, $$r = \sqrt{(x-x_0)^2 + (y-y_0)^2} \quad (A1a)$$

gives the radial distance of a point (x, y) on the surface from the centre of the cup. Parameter $r_e$ is used to make the cup elliptical in shape, and is given by $$r_e = \frac{r_0(1 - e^2)}{\sqrt{1 + e^2 + 2e\cos 2(\theta - \theta_0)}} \quad (A2)$$

where $$\theta = \tan^{-1}\left(\frac{y - y_0}{x - x_0}\right) \quad (A2a)$$

and $r_0$ gives the mean radius of the cup. The two new parameters, e and $\theta_e$ describe the amount of elongation and the angle of elongation respectively. For example, ff $\theta_e=90°$ and 0<e<1, the cup is elongated in the vertical direction. If $e_1=0$, the cup is circular, and the equations reduce to those already described.

This model can be fit to images using the methods already described to provide initial estimates of parameter values. A suitable initial guess for $\theta_e$ is 90°, and e can be set close to, but not exactly, 0 (e.g. 0.01). Levenburg-Marquardt least-squares optimisation can be used to refine the parameter estimates. Tests with the data set described in the main section show a) the goodness-of-fit of the elliptical model is better than that obtained with the circular model b) that e is greater in the glaucoma group (i.e. the cup tends to be more elongated), consistent with a greater degree of excavation in the superior and inferior poles, and c) the angle of elongation is closer to vertical in the glaucoma group.

In some embodiments, finding the best-fitting model parameters for each image requires the application of iterative non-linear least-squares optimisation, which is not guaranteed to work in all cases (see Press et al., 1994 for discussion). Although this example uses a method (Leven-burg-Marquardt) which is believed to be one of the most efficient, it, like all similar procedures, requires a good initial estimate of the parameters which are to be adjusted if it is to work properly. In the sample of images in this example, the method almost always (198 out of 200 cases) converged on an acceptable solution. The two images in which the method failed were both from normal eyes in which a cup was barely perceptible. Such cases can be detected either by visual inspection or by first fitting a function lacking a cup i.e. by calculating $f_p$.

Alternative models may be adapted to provide an estimate that is directly related to disc area. Some of the parameters of the model function do correlate with the HRT measure of area (ag: Table 5) but these correlations may be indirect. Disc area itself is not affected in glaucoma (Jonas et al., Graefes Arch Clin Exp Ophthalmol. 226:531–538 (1988); lester et al., J Glaucoma. 6:371–376 (1997d)), however cup area and disc area are strongly correlated in normal eyes (Teal et al., (1972); Bengtsson, (1976); Britton et al., (1987)) and the model's measure of cup size may therefore be adapted to be accompanied by an estimate of disc area and re-expressed as a ratio.

The classification method of this example is based on the assumption that the data values in each group are distributed according to a multivariate normal distribution. Other classification methods could be used, e.g. back propagation neural nets (Parfitt et al., Invest Ophthalmol Vis Sci Suppl. 36:S628 (1995); Brigatti et al., (1996)) which might perform better than the method of the example.

In some embodiments, validation of the accuracy of the classification method may depend on the selection of subjects for the control normal and test groups (such as the glaucoma group). For example, the normal subject group may be an unbiased sample of a glaucoma-free population; while the subjects in the glaucoma group may be an unbiased sample of the glaucoma population, and may have early visual field damage.

The two parameters showing the largest difference (in statistical terms) between the two groups in the present example were horizontal and vertical image curvature (c and d). Positive values of these indices mean that the neuroretinal rim region around the cup is convexly curved, i.e. that it bulges upwards into the vitreous.

Curvature values were greatly reduced in the glaucoma patients, while a negative correlation between c and d, and disc area (ag) (r=–0.34 and –0.30 respectively) was also observed. The horizontal component of curvature was greater than the vertical component in normal ONH images. The steepness of the cup walls was measured as $g_r$ (cup gradient measure) and showed a statistically large difference between groups. We defined $g_r$ in terms of the component of the gradient measured in a direction radial to the centre of the cup. Initial measurements showed that although similar, non-component, measures were significantly greater in the glaucoma group, measures based on the radial component differed more. The gradient measure was divided into nasal and temporal components, and the present results show that in normal images the nasal component was greater on average than the temporal component, and the temporal component was more severely affected by glaucoma. Cup radius ($r_0$) and cup depth ($z_{max}$) were both increased in the glaucoma group. Cup size may be more informative if expressed as a ratio with disc size. In cup depth measures, $z_{max}$ differed less between the groups than did the alternative measure ($z_{500}$) which was an average of the 500 most extreme depth values within the cup region. Slant in the naso-temporal axis showed a significant difference between the two groups. Normal images tended to be slanted, by about 6° (=−0.098 mm/mm) on average, in such a way that the temporal (foveal) side is higher than the nasal side. This slant was absent, on average, in the glaucoma group.

In alternative embodiments, parameters may be used in accordance with the present invention as diagnostic indicators of glaucoma, where the parameters are selected from the group consisting of: horizontal Image curvature; vertical image curvature; nasotemporal slant; fit of the model to the image; cup gradient measure; cup gradient measure temporal; cup gradient measure nasal; and, fit of parabolic function; and parameters e and theta (degree of cup elongation and the angle of elongation). In alternative embodiments, such parameters may be selected from the group consisting of: cup radius; cup depth; and, maximum cup depth.

What is claimed is:

1. A method of characterizing an optic nerve head, the method comprising the steps of:
    a) acquiring a topographic image of the optic nerve head;
    b) defining a topographic model fitted to the topographic image of the optic nerve head about a centre of analysis, wherein the centre of analysis is identified on the optic nerve head, and wherein the topographic model is defined using model morphological parameters and comprises a parabolic surface;
    c) applying the topographic model to identify a cup region on the topographic image of the optic nerve head by comparing the acquired topographic image to the parabolic surface, wherein the cup region comprises the centre of analysis of the optic nerve head;
    d) excluding the cup region from the acquired image and refitting the parabolic surface to the acquired image; and
    e) modeling the shape of the cup superimposed on the model parabolic surface, to define the topographic model of the optic nerve head.

2. The method of claim 1, wherein the topographic model is fitted to the topographic image by applying the formula:

$$f = \left\{ \frac{1}{N} \sum_{i,j}^{allpixels} [\gamma I(i,j) - z(\alpha i, \beta j)]^2 \right\}^{\frac{1}{2}}$$

wherein:
  I (i, j) is the value of the image at pixel (i, j);
  N is the total number of pixels in the image; and
  $\alpha$, $\beta$ and $\gamma$ are constants that may be used to adjust scales.

3. The method of claim 1, further comprising comparing one or more of the model morphological parameters to one or more corresponding predetermined morphological parameters obtained from one or more control topographic images.

4. The method of claim 1, wherein the model morphological parameters are used to calculate one or more model morphological indices for comparison to one or more corresponding predetermined morphological indices obtained from one or more control topographic images.

5. The method of claim 4 wherein the model morphological indices are selected from the group consisting of: horizontal Image curvature; vertical image curvature; nasotemporal slant; fit of the model to the image; cup gradient measure; cup gradient measure temporal; cup gradient measure nasal; fit of parabolic function; e (degree of cup elongation); and, theta (angle of elongation).

6. The method of claim 1, wherein the method is implemented in a computer.

7. The method of claim 1 wherein the topographic model comprises applying the formula:

$$z(x,y) = \frac{z_m}{1 + e^{(r-r_0)/s}} + a(x-x_0) + b(y-y_0) + c(x-x_0)^2 + d(y-y_0)^2 + z_0$$

where $r = \sqrt{(x-x_0)^2 + (y-y_0)^2}$ wherein the depth of a surface, z, is defined as a function of position (x, y) on the surface, the surface being centered on position ($x_0$, $y_0$); and,
  $\alpha$ is a parameter defining an optic nerve head slant in the x direction;
  b is a parameter defining an optic nerve head slant in the y direction;
  c is a parameter defining an optic nerve head curvature in the x direction;
  d is a parameter defining an optic nerve head curvature in the y direction;
  $z_0$ is a parameter defining a constant surface offset in the z direction;
  s is a parameter defining a cup slope;
  $z_m$ is a parameter defining a cup depth; and,
  r is a parameter defining a cup width.

8. A method of characterizing an optic nerve head, the method comprising the steps of:
    a) acquiring a topographic image of the optic nerve head;
    b) defining a topographic model fitted to the topographic image of the optic nerve head about a centre of analysis, wherein the centre of analysis is identified on the optic nerve head, and wherein the topographic model is defined using model morphological parameters and comprises a parabolic surface;
    c) applying the topographic model to identify a cup region on the topographic image of the optic nerve head by comparing the acquired topographic image to the parabolic surface, wherein the cup region comprises the centre of analysis of the optic nerve head;
    wherein the topographic model comprises applying the formula:

$$z(x,y) = \frac{z_m}{1 + e^{(r-r_0)/s}} + a(x-x_0) + b(y-y_0) + c(x-x_0)^2 + d(y-y_0)^2 + z_0$$

where $r = \sqrt{(x-x_0)^2 + (y-y_0)^2}$ wherein the depth of a surface, z, is defined as a function of position (x, y) on the surface, the surface being centered on position ($x_0$, $y_0$); and,
  $\alpha$ is a parameter defining an optic nerve head slant in the x direction;
  b is a parameter defining an optic nerve head slant in the y direction;
  c is a parameter defining an optic nerve head curvature in the x direction;
  d is a parameter defining an optic nerve head curvature in the y direction;
  $z_0$ is a parameter defining a constant surface offset in the z direction;
  s is a parameter defining a cup slope;

$z_m$ is a parameter defining a cup depth; and,
r is a parameter defining a cup width.

9. The method of claim 8, further comprising the steps of:
a) excluding the cup region from the acquired image and refitting the parabolic surface to the acquired image; and
b) modeling the shape of the cup superimposed on the model parabolic surface, to define the topographic model of the optic nerve head.

10. The method of claim 8, further comprising calculating a least-squares fit of the parabolic surface to the acquired image by adjusting parameters $\alpha$, b, CJ d and $z_0$.

* * * * *